(12) United States Patent
Winter et al.

(10) Patent No.: US 8,389,724 B2
(45) Date of Patent: Mar. 5, 2013

(54) CRYSTALLINE SALT FORMS OF A 5,6,7,8-TETRAHYDRO-1,2,4-TRIAZOLO[4,3-A]PYRAZINE DERIVATIVE

(75) Inventors: Stephen Benedict David Winter, Barcelona (ES); Monica Benito Velez, Barcelona (ES); Ernesto Duran Lopez, Barcelona (ES)

(73) Assignee: Corporacion Medichem, S.L., Barcelona (ES)

( * ) Notice: Subject to any disclaimer, the term of this patent is extended or adjusted under 35 U.S.C. 154(b) by 0 days.

(21) Appl. No.: 13/433,629

(22) Filed: Mar. 29, 2012

(65) Prior Publication Data

US 2012/0184558 A1    Jul. 19, 2012

Related U.S. Application Data

(63) Continuation of application No. 12/511,503, filed on Jul. 29, 2009, now abandoned.

(60) Provisional application No. 61/137,428, filed on Jul. 29, 2008, provisional application No. 61/137,429, filed on Jul. 29, 2008.

(51) Int. Cl.
*C07D 471/00*     (2006.01)

(52) U.S. Cl. ........................................ 544/350
(58) Field of Classification Search .................. 544/350
See application file for complete search history.

(56) References Cited

U.S. PATENT DOCUMENTS 6,699,871 B2 *   3/2004   Edmondson et al. ......... 514/249
2010/0069637 A1   3/2010   Winter et al.

FOREIGN PATENT DOCUMENTS

| WO | WO 2005/072530 | * | 8/2005 |
| WO | WO 2008/070692 | * | 6/2008 |
| WO | WO 2010/000469 A2 | | 1/2010 |
| WO | WO 2010/092090 A2 | | 8/2010 |
| WO | WO 2010/117738 A2 | | 10/2010 |

OTHER PUBLICATIONS

Berge, et al. Journal of Pharmaceutical Sciences, 66(1), 1977, 1-19.*

* cited by examiner

*Primary Examiner* — Douglas M Willis
(74) *Attorney, Agent, or Firm* — Cozen O'Connor

(57) ABSTRACT

This invention provides a novel crystalline sitagliptin ethanedisulfonate salt having the structure set forth below, and a method for using same to treat type 2 diabetes.

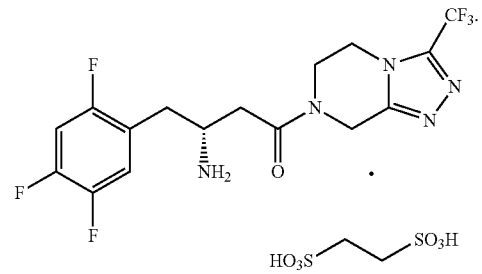

2 Claims, 9 Drawing Sheets

X-RAY POWDER DIFFRACTOGRAM OF SITAGLIPTIN GALACTARATE

X-RAY POWDER DIFFRACTOGRAM OF SITAGLIPTIN HEMI-L-MALATE

X-RAY POWDER DIFFRACTOGRAM OF SITAGLIPTIN D-GLUCONATE

X-RAY POWDER DIFFRACTOGRAM OF SITAGLIPTIN SUCCINATE

X-RAY POWDER DIFFRACTOGRAM OF SITAGLIPTIN HYDROBROMIDE

X-RAY POWDER DIFFRACTOGRAM OF SITAGLIPTIN THIOCYANATE

X-RAY POWDER DIFFRACTOGRAM OF SITAGLIPTIN OXALATE

X-RAY POWDER DIFFRACTOGRAM OF SITAGLIPTIN L-ASPARTATE

X-RAY POWDER DIFFRACTOGRAM OF SITAGLIPTIN ETHANEDISULFONATE

X-RAY POWDER DIFFRACTOGRAM OF SITAGLIPTIN (S)-PYROGLUTAMATE

X-RAY POWDER DIFFRACTOGRAM OF SITAGLIPTIN GLUTARATE

X-RAY POWDER DIFFRACTOGRAM OF SITAGLIPTIN ACETATE

X-RAY POWDER DIFFRACTOGRAM OF SITAGLIPTIN HYDROCHLORIDE IN AMORPHOUS FORM

X-RAY POWDER DIFFRACTOGRAM OF SITAGLIPTIN CITRATE IN AMORPHOUS FORM

X-RAY POWDER DIFFRACTOGRAM OF SITAGLIPTIN HEMICITRATE IN AMORPHOUS FORM

X-RAY POWDER DIFFRACTOGRAM OF SITAGLIPTIN GLYCOLATE IN AMORPHOUS FORM

X-RAY POWDER DIFFRACTOGRAM OF SITAGLIPTIN MALATE IN AMORPHOUS FORM

CRYSTALLINE SALT FORMS OF A 5,6,7,8-TETRAHYDRO-1,2,4-TRIAZOLO[4,3-A]PYRAZINE DERIVATIVE

PRIORITY

This application is a continuation of U.S. application Ser. No. 12/511,503, filed Jul. 29, 2009 now abandoned, which claims priority from U.S. Provisional Applications No. 61/137,428 and 61/137,429, both filed on Jul. 29, 2008, the contents of each of which are herein incorporated by reference in their entirety.

FIELD OF THE INVENTION

The present invention relates generally to novel crystalline salt forms of 7-[(3R)-3-amino-1-oxo-4-(2,4,5-trifluorophenyl)butyl]-5,6,7,8-tetrahydro-3-(trifluoromethyl)-1,2,4-triazolo[4,3-a]pyrazine, i.e. sitagliptin, to processes for their preparation and isolation, and to pharmaceutical compositions comprising the same.

BACKGROUND OF THE INVENTION

Sitagliptin (Compound I) is the international commonly accepted name for 7-[(3R)-3-amino-1-oxo-4-(2,4,5-trifluorophenyl)butyl]-5,6,7,8-tetrahydro-3-(trifluoromethyl)-1,2,4-triazolo[4,3-a]pyrazine (which is also known as (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine), and has an empirical formula of $C_{16}H_{15}F_6N_5O$ and a molecular weight of 407.31.

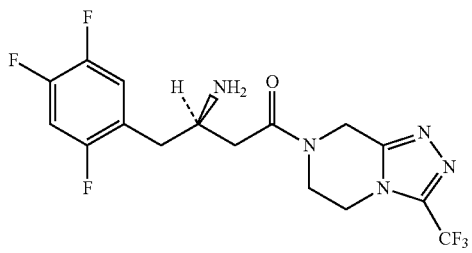

(I)

The phosphate salt of sitagliptin has been selected for medical purposes since has been proved to be useful for the treatment of diabetes. Sitagliptin phosphate is a selective inhibitor of dipeptidyl peptidase IV which lowers blood sugar levels in patients with Type 2 diabetes, also known as non-insulin dependent diabetes mellitus. In the United States, sitagliptin phosphate is marketed under the name Januvia™ for the treatment of Type 2 diabetes.

Sitagliptin phosphate salt and different forms thereof have been disclosed in a number of references (i.e. U.S. Pat. No. 7,326,708, and U.S. Patent Application Nos. 20060287528, 20070021430 and 20070281941).

Sitagliptin base and its pharmaceutically acceptable acid addition salts have been described in U.S. Pat. No. 6,699,871. In particular, Example 7 of U.S. Pat. No. 6,699,871 discloses the preparation of sitagliptin base and its hydrochloride salt.

Different salt forms of the same pharmaceutically active moiety differ in their physical properties such as melting point, solubility, etc. These properties may appreciably influence pharmaceutical properties such as dissolution rate and bioavailability. In addition, polymorphism, which is defined as the ability of a substance to crystallize in more than one crystal lattice arrangement, can also influence many aspects of solid state properties of a drug. Different crystal modifications of a substance may differ considerably from one another in many respects such as their solubility, dissolution rate and finally bioavailability.

In this regard, International Patent Publication No. WO 05/072530 described several novel crystalline salts of sitagliptin, i.e. the hydrochloric acid, tartaric acid, benzenesulfonic acid, p-toluenesulfonic acid, and 10-camphorsulfonic acid crystalline salts. In addition, the hemifumarate salt of sitagliptin has been described by D. Kim et al. in *J. Med. Chem.* 2005, 48, 141-151. Also, International Patent Publication No. WO 07/035198 relates to a crystalline anhydride form of the dodecylsulfate salt of sitagliptin. Furthermore, International Patent Publication No. WO 08/000418 discloses the preparation of sitagliptin hydrochloride in amorphous form. In addition, International Patent Publication No. WO 09/085990 describes other acid addition salts of sitagliptin, i.e. sitagliptin salts of di-p-tolyl-L-tartaric acid, phosphoric acid, sulfuric acid, hydrobromic acid, methanesulfonic acid, acetic acid, benzoic acid, oxalic acid, succinic acid, mandelic acid, fumaric acid, and lactic acid.

In view of the foregoing, it would be desirable to provide new salt forms of sitagliptin. Further, it would be desirable to have reliable processes for producing these salt forms of sitagliptin. Additionally, the various salt forms of sitagliptin could be used to prepare improved pharmaceutical compositions.

SUMMARY OF THE INVENTION

The present invention relates generally to novel crystalline salt forms of 7-[(3R)-3-amino-1-oxo-4-(2,4,5-trifluorophenyl)butyl]-5,6,7,8-tetrahydro-3-(trifluoromethyl)-1,2,4-triazolo[4,3-a]pyrazine, i.e. sitagliptin, to processes for their preparation and isolation, and to pharmaceutical compositions comprising the same.

DETAILED DESCRIPTION OF THE INVENTION

It has been found that sitagliptin can exist in a number of crystalline salt forms.

The novel salt forms of sitagliptin have been prepared and structurally characterized as described herein and are referred to herein as sitagliptin galactarate crystalline form (Form I), sitagliptin hemi-L-malate crystalline form (Form I), sitagliptin D-gluconate crystalline form (Form I), sitagliptin succinate crystalline form (Form I), sitagliptin hydrobromide crystalline form (Form I), sitagliptin thiocyanate crystalline form (Form I), sitagliptin oxalate crystalline form (Form I), sitagliptin L-aspartate crystalline form (Form I), sitagliptin ethanedisulfonate crystalline form (Form I), sitagliptin pyroglutamate crystalline form (Form I), sitagliptin glutarate crystalline form (Form I), and sitagliptin acetate crystalline form (Form I).

The solid crystalline salt forms of sitagliptin of the present invention have been characterized by means of Powder X-ray diffraction pattern (XRD).

In addition, a selected group of the novel crystalline salt forms of sitagliptin of the present invention have been found to be highly stable in terms of polymorphic form after 10 months of storage, which makes them suitable for pharmaceutical formulation use.

Further, some of the selected crystalline salt forms of sitagliptin of the present invention exhibit a good solubility profile in water, i.e. equal to or higher than 20 g/L, and hence also show enhanced pharmaceutical properties regarding the dissolution rate and bioavailability.

Additionally, the formation of the selected crystalline salt forms of sitagliptin of the invention might be an efficient way of purifying sitagliptin base.

It has also been found that sitagliptin can exist in a number of amorphous salt forms.

The novel amorphous salt forms of sitagliptin have been prepared and structurally characterized as described herein and are referred to herein as sitagliptin citrate amorphous form, sitagliptin hemicitrate amorphous form, sitagliptin glycolate amorphous form, and sitagliptin L-malate amorphous form.

The solid amorphous salt forms of sitagliptin of the present invention have been characterized by means of Powder X-ray diffraction pattern (XRD).

A first aspect of the present invention includes a new sitagliptin galactarate salt in crystalline form (designated herein as Form I).

Figure 1:
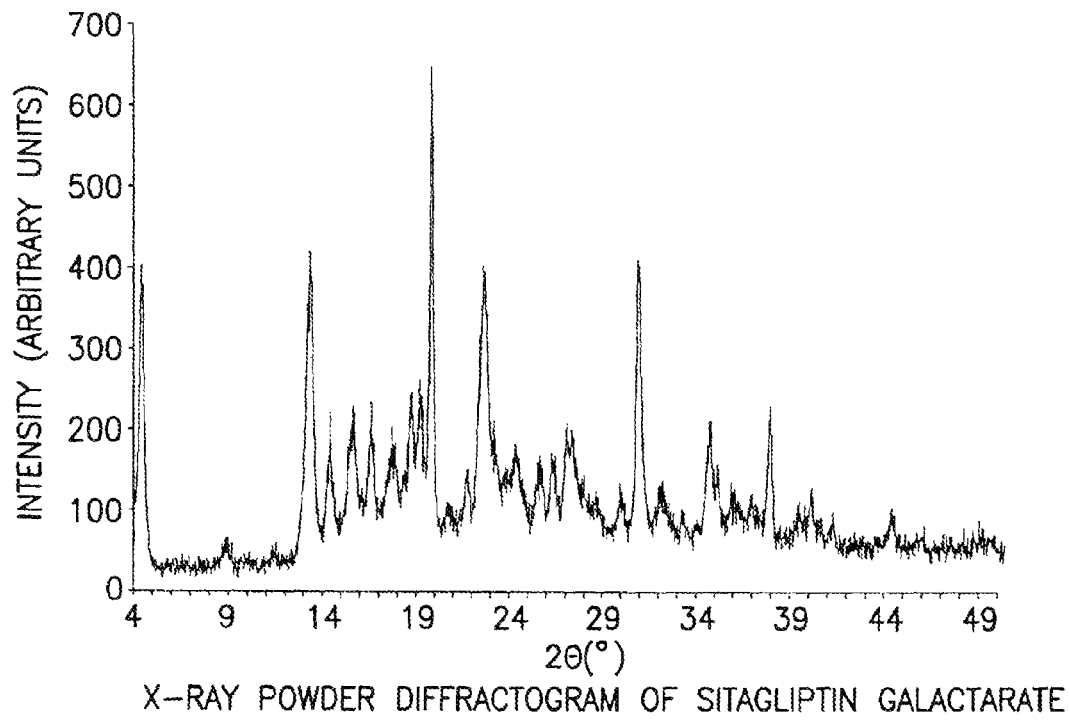
FIG. 1 illustrates the X-ray powder diffraction pattern (XRD) of sitagliptin galactarate.

The sitagliptin galactarate Form I of the present invention shows an XRD pattern (2θ) having characteristic peaks at approximately 4.4, 13.2, 19.6, 22.4 and 30.7° and with further peaks at: 14.3, 15.5, 16.5, 17.5, 18.6, 19.0, 23.0, 24.1, 25.4, 26.0, 26.9, 27.1, 34.5 and 37.7°. FIG. 1 illustrates the XRD of sitagliptin galactarate crystalline Form I.

The sitagliptin galactarate Form I of the present invention has been found to be highly stable in terms of polymorphic form after ten months of storage. Also, after ten months of storage, the sitagliptin galactarate Form I of the invention has been found to show an off-white colour and a purity higher than about 99.1%, as determined by HPLC. Further, the sitagliptin galactarate Form I of the invention is sparingly soluble in water (i.e. solubility about 20 g/L).

Another aspect of the invention relates to a process for preparing sitagliptin galactarate Form I, said process comprising contacting sitagliptin with galactaric acid, optionally in the presence of a suitable solvent, and removing the solvent when necessary.

The suitable solvent comprises a $C_1$-$C_5$ alcohol solvent or mixtures thereof. Preferably, the $C_1$-$C_5$ alcohol solvent is 2-propanol.

The 1:1 salt correlation of sitagliptin galactarate was confirmed by $^1$H NMR spectrum.

Another aspect of the present invention includes a new sitagliptin hemi-L-malate salt in crystalline form (designated herein as Form I).

Figure 2:
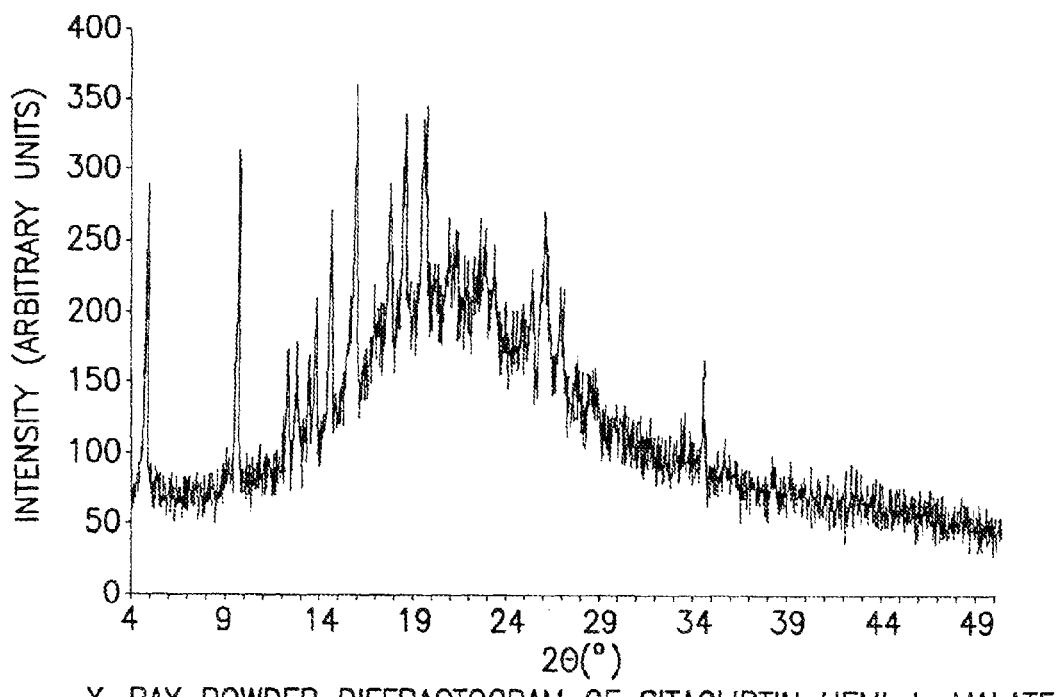
FIG. 2 illustrates the X-ray powder diffraction pattern (XRD) of sitagliptin hemi-L-malate.

The sitagliptin hemi-L-malate Form I of the present invention shows an XRD pattern (2θ) having characteristic peaks at approximately 4.7, 9.5, 14.3, 15.6, 17.4, 18.2, 19.3 and 25.6° and with further peaks at: 12.1, 12.6, 13.3, 13.6, 25.0, 26.6 and 34.3°. FIG. 2 illustrates the XRD of sitagliptin hemi-L-malate crystalline Form I.

Another aspect of the invention relates to a process for preparing sitagliptin hemi-L-malate Form I, said process comprising contacting sitagliptin with not more than 0.5 molar equivalents of L-malic acid, optionally in the presence of a suitable solvent, and removing the solvent when necessary.

The suitable solvent comprises a $C_1$-$C_5$ alcohol solvent or mixtures thereof. Preferably, the $C_1$-$C_5$ alcohol solvent is 2-propanol.

The 2:1 salt correlation of sitagliptin L-hemimalate was confirmed by $^1$H NMR spectrum.

Another aspect of the present invention includes a new sitagliptin D-gluconate salt in crystalline form (designated herein as Form I).

Figure 3:
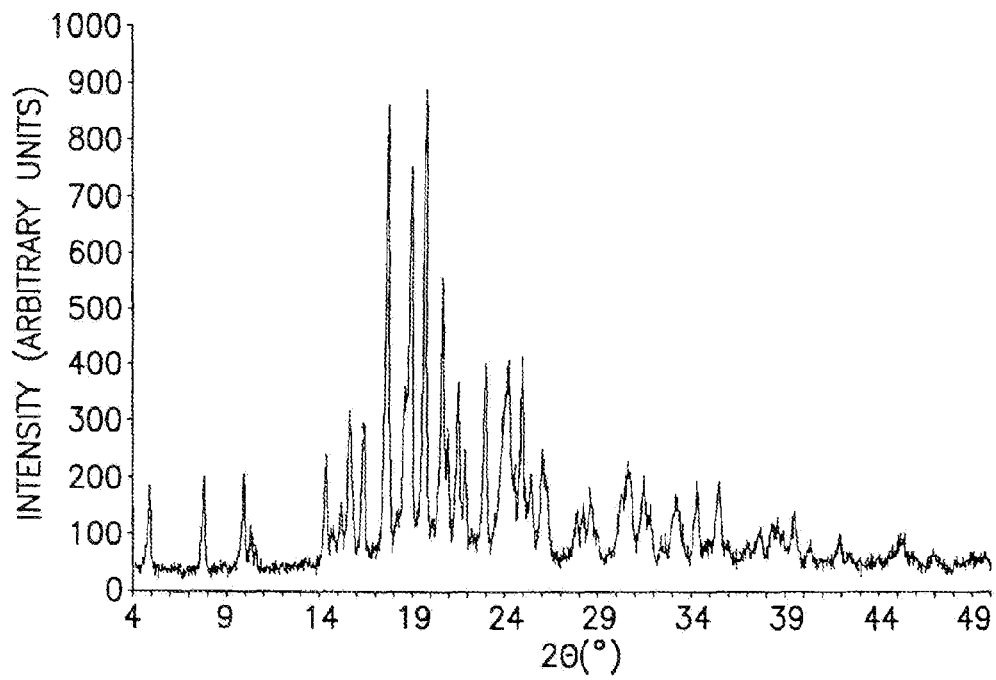
FIG. 3 illustrates the X-ray powder diffraction pattern (XRD) of sitagliptin D-gluconate.

The sitagliptin D-gluconate Form I of the present invention shows an XRD pattern (2θ) having characteristic peaks at approximately 15.7, 16.4, 17.6, 18.6, 18.9, 19.6, 20.6, 20.9, 21.5, 22.9, 24.2 and 24.9° and with further peaks at: 5.0, 7.9; 10.0, 14.4, 15.2, 21.8, 24.5, 25.4, 26.0, 27.9, 28.3, 28.6, 30.6, 31.5, 31.9, 33.2, 34.3, 35.5 and 39.5°. FIG. 3 illustrates the XRD of sitagliptin D-gluconate crystalline Form I.

Another aspect of the invention relates to a process for preparing sitagliptin D-gluconate Form I, said process comprising contacting sitagliptin with D-gluconic acid, optionally in the presence of a suitable solvent, and removing the solvent when necessary.

The suitable solvent comprises a $C_1$-$C_5$ alcohol solvent or mixtures thereof. Preferably, the $C_1$-$C_5$ alcohol solvent is 2-propanol.

The 1:1 salt correlation of sitagliptin D-gluconate was confirmed by $^1$H NMR spectrum.

Another aspect of the present invention includes a new sitagliptin succinate salt in crystalline form (designated herein as Form I).

Figure 4:
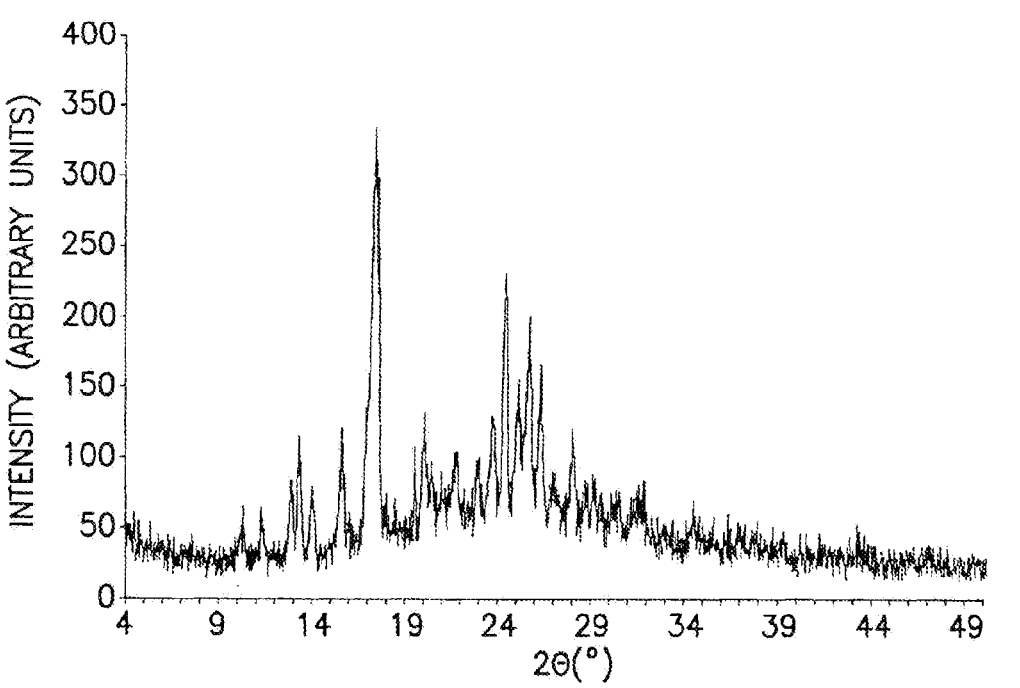
FIG. 4 illustrates the X-ray powder diffraction pattern (XRD) of sitagliptin succinate.

The sitagliptin succinate Form I of the present invention shows an XRD pattern (2θ) having characteristic peaks at approximately 13.4, 15.7, 17.3, 20.0, 23.7, 24.4, 25.1, 25.6, 26.2 and 27.9° and with further peaks at: 13.0, 13.0, 14.1, 19.5, 20.4, 21.8 and 23.0°. FIG. 4 illustrates the XRD of sitagliptin succinate crystalline Form I.

Another aspect of the invention relates to a process for preparing sitagliptin succinate Form I, said process comprising contacting sitagliptin with succinic acid, optionally in the presence of a suitable solvent, and removing the solvent when necessary.

The suitable solvent comprises a $C_1$-$C_5$ alcohol solvent or mixtures thereof. Preferably, the $C_1$-$C_5$ alcohol solvent is 2-propanol.

The 1:1 salt correlation of sitagliptin succinate was confirmed by $^1$H NMR spectrum.

Another aspect of the present invention includes a new sitagliptin hydrobromide salt in crystalline form (designated herein as Form I).

Figure 5:
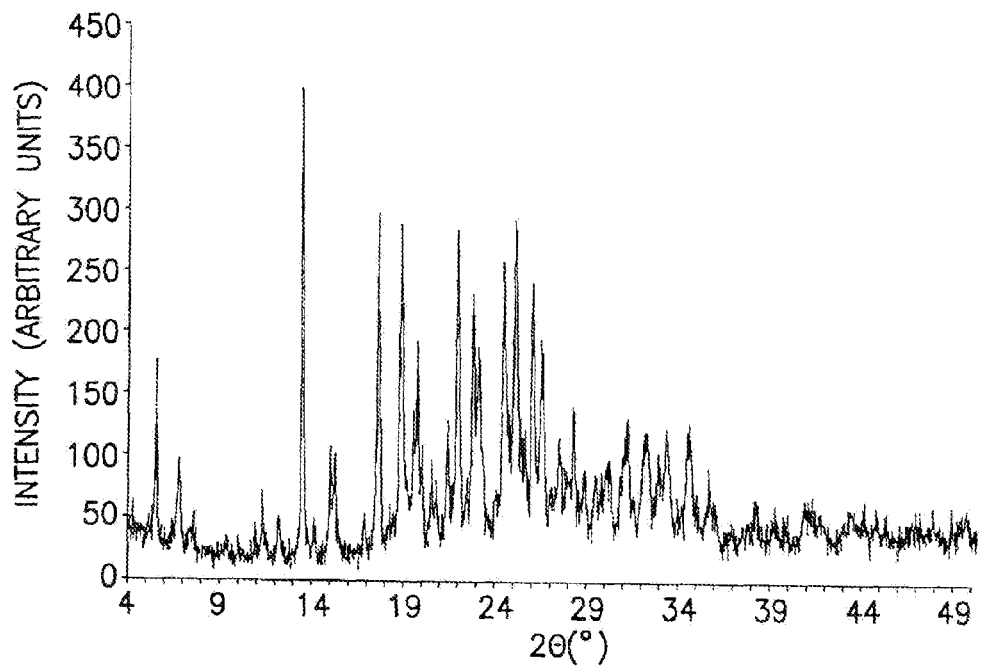
FIG. 5 illustrates the X-ray powder diffraction pattern (XRD) of sitagliptin hydrobromide.

The sitagliptin hydrobromide Form 1 of the present invention shows an XRD pattern (2θ) having characteristic peaks at approximately 5.6, 13.4, 17.6, 18.8, 19.7, 19.7, 21.9, 22.7, 23.0, 24.4, 25.0, 25.9 and 26.4° and with further peaks at: 6.9, 15.0, 15.2, 20.0, 20.5, 21.3, 25.3, 25.5, 27.4, 28.1, 31.1, 32.1, 32.2, 33.3 and 34.4°. FIG. 5 illustrates the XRD of sitagliptin hydrobromide crystalline Form I.

Another aspect of the invention relates to a process for preparing sitagliptin hydrobromide Form I, said process comprising contacting sitagliptin with hydrobromic acid, optionally in the presence of a suitable solvent, and removing the solvent when necessary.

The suitable solvent comprises a $C_1$-$C_5$ alcohol solvent or mixtures thereof. Preferably, the $C_1$-$C_5$ alcohol solvent is 2-propanol.

Another aspect of the present invention includes a new sitagliptin thiocyanate salt in crystalline form (designated herein as Form I).

Figure 6:
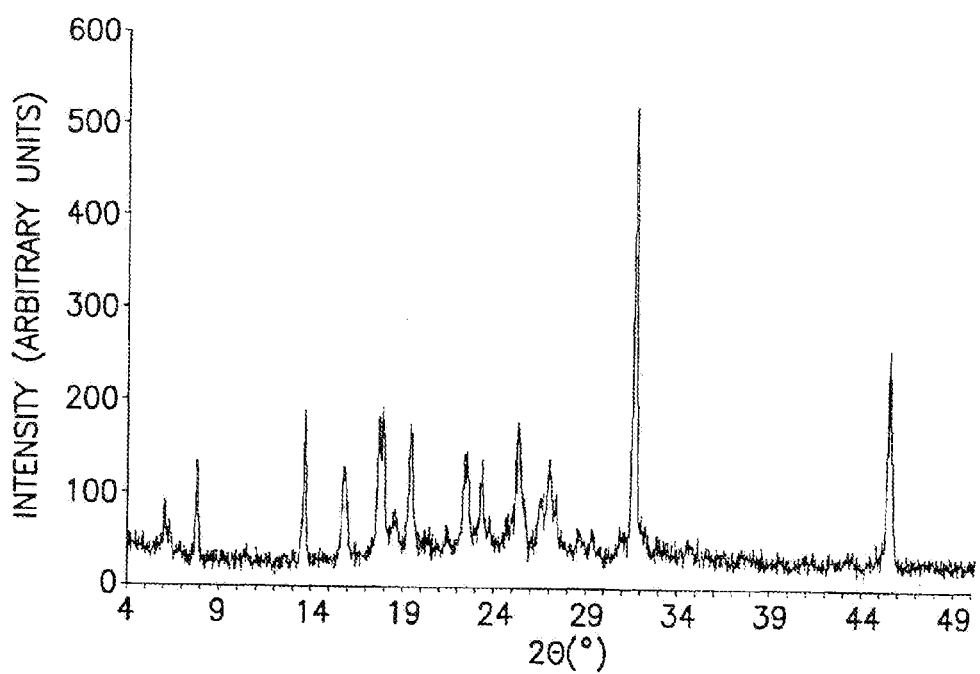
FIG. 6 illustrates the X-ray powder diffraction pattern (XRD) of sitagliptin thiocyanate.

The sitagliptin thiocyanate Form I of the present invention shows an XRD pattern (2θ) having characteristic peaks at approximately 7.9, 13.7, 15.8, 17.7, 17.9, 19.4, 22.4, 22.5, 23.3, 25.2, 25.3, 26.9, 31.7 and 45.4° and with further peaks at: 6.2, 26.5 and 27.3°. FIG. 6 illustrates the XRD of sitagliptin thiocyanate crystalline Form I.

The sitagliptin thiocyanate Form I of the present invention has been found to be highly stable in terms of polymorphic form after ten months of storage. Also, after ten months of storage, the sitagliptin thiocyanate Form I of the invention has been found to show a light pink colour and a purity higher than about 99.2%, as determined by HPLC.

Another aspect of the invention relates to a process for preparing sitagliptin thiocyanate Form I, said process comprising contacting sitagliptin with thiocyanic acid, optionally in the presence of a suitable solvent, and removing the solvent when necessary.

The suitable solvent comprises a $C_1$-$C_5$ alcohol solvent or mixtures thereof. Preferably, the $C_1$-$C_5$ alcohol solvent is 2-propanol.

The thiocyanic acid can be optionally prepared in situ from sodium thiocyanate and hydrochloric acid.

Another aspect of the present invention includes a new sitagliptin oxalate salt in crystalline form (designated herein as Form I).

Figure 7:
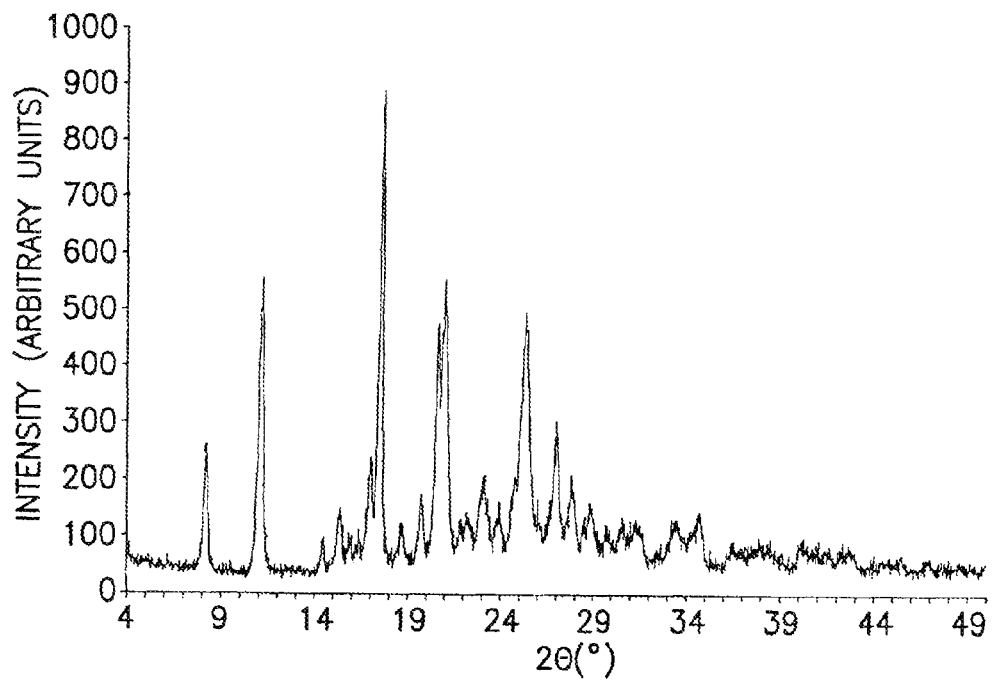
FIG. 7 illustrates the X-ray powder diffraction pattern (XRD) of sitagliptin oxalate.

The sitagliptin oxalate Form I of the present invention shows an XRD pattern (2θ) having characteristic peaks at approximately 8.3, 11.1, 17.0, 17.5, 20.6, 20.9, 25.3 and 27.0° and with further peaks at: 14.5, 15.3, 15.4, 18.6, 19.7, 23.1, 24.0, 24.8, 27.8, 28.9 and 34.7°. FIG. 7 illustrates the XRD of sitagliptin oxalate crystalline Form I.

Another aspect of the invention relates to a process for preparing sitagliptin oxalate Form I, said process comprising contacting sitagliptin with oxalic acid, optionally in the presence of a suitable solvent, and removing the solvent when necessary.

The suitable solvent comprises a $C_1$-$C_5$ alcohol solvent or mixtures thereof. Preferably, the $C_1$-$C_5$ alcohol solvent is 2-propanol.

Another aspect of the present invention includes a new sitagliptin L-aspartate salt in crystalline form (designated herein as Form I).

Figure 8:
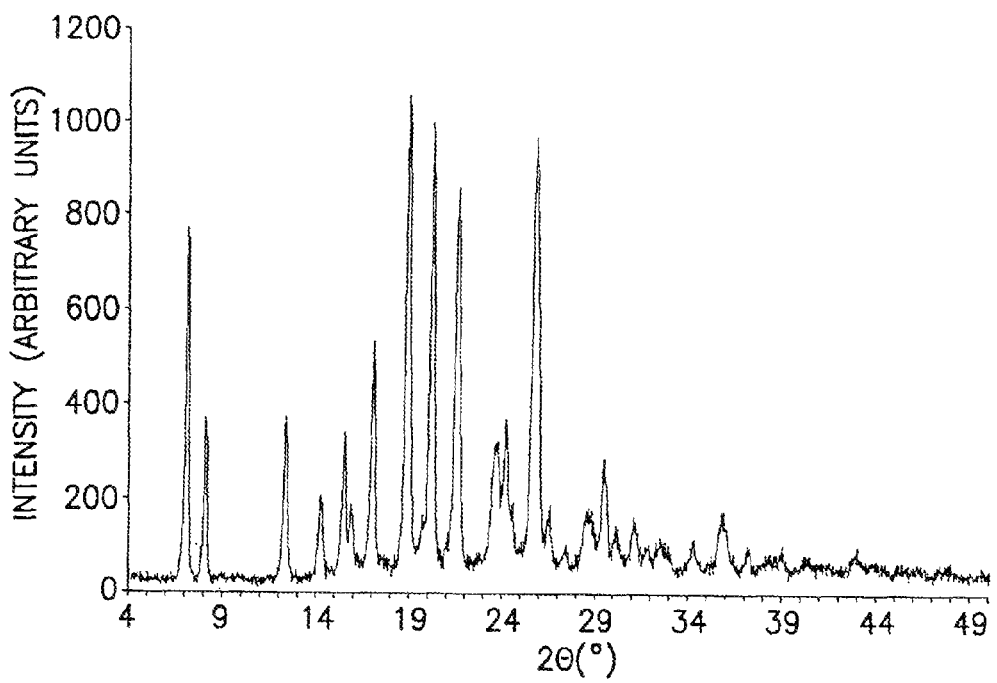
FIG. 8 illustrates the X-ray powder diffraction pattern (XRD) of sitagliptin aspartate.

The sitagliptin L-aspartate Form I of the present invention shows an XRD pattern (2θ) having characteristic peaks at approximately 7.1, 8.1, 12.2, 15.4, 16.9, 18.7, 20.0, 21.1, 21.4, 23.6, 24.0, 25.6 and 29.4° and with further peaks at: 14.1, 15.7, 19.5, 26.4, 28.5, 30.0, 31.0 and 35.8°. FIG. 8 illustrates the XRD of sitagliptin L-aspartate crystalline Form I.

Another aspect of the invention relates to a process for preparing sitagliptin L-aspartate Form I, said process comprising contacting sitagliptin with L-aspartic acid, optionally in the presence of a suitable solvent, and removing the solvent when necessary.

The suitable solvent comprises a $C_1$-$C_5$ alcohol solvent or mixtures thereof. Preferably, the $C_1$-$C_5$ alcohol solvent is 2-propanol.

The 1:1 salt correlation of sitagliptin L-aspartate was confirmed by $^1$H NMR spectrum.

Another aspect of the present invention includes a new sitagliptin ethanedisulfonate salt in crystalline form (designated herein as Form I).

Figure 9:
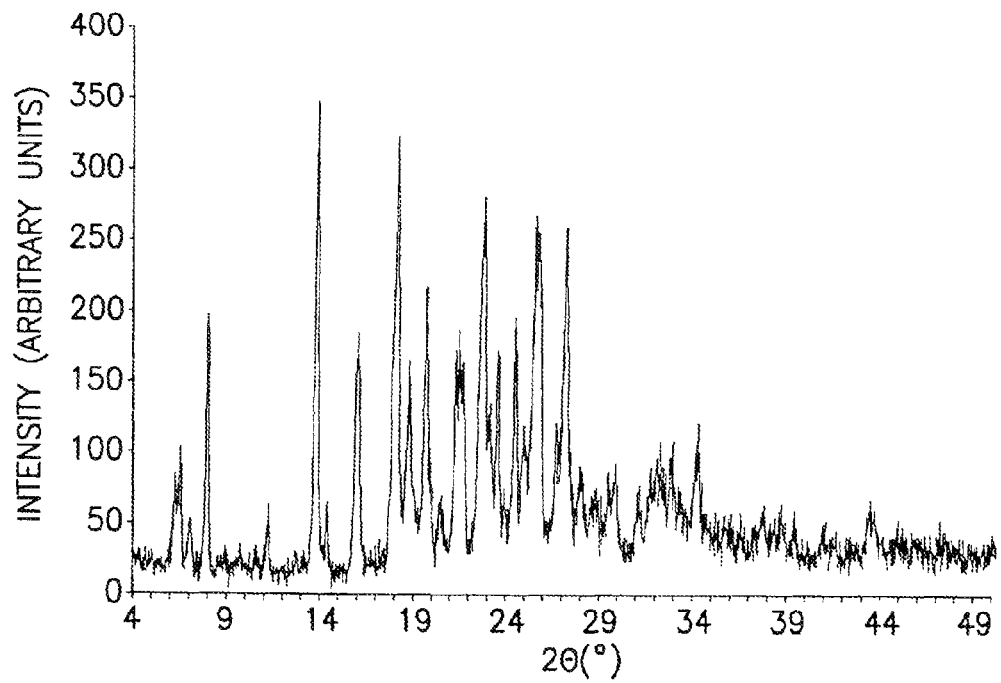
FIG. 9 illustrates the X-ray powder diffraction pattern (XRD) of sitagliptin ethanedisulfonate.

The sitagliptin ethanedisulfonate Form I of the present invention shows an XRD pattern (2θ) having characteristic peaks at approximately 8.0, 13.8, 16.0, 18.0, 18.7, 19.6, 21.2, 21.4, 21.6, 22.7, 23.5, 24.4, 25.4, 25.6 and 27.1° and with further peaks at: 6.3, 6.6, 7.1, 11.2, 14.4, 20.4, 23.0, 24.8, 26.5, 27.9 and 34.7°. FIG. 9 illustrates the XRD of sitagliptin ethanedisulfonate crystalline Form I.

The sitagliptin ethanedisulfonate Form I of the present invention has been found to be highly stable in terms of polymorphic form after ten months of storage. Also, after ten months of storage, the sitagliptin ethanedisulfonate Form I of the invention has been found to show an off-white colour and a purity higher than about 99.8%, as determined by HPLC. Further, the sitagliptin ethanedisulfonate Form I of the invention is freely soluble in water (i.e. solubility>300 g/L).

Another aspect of the invention relates to a process for preparing sitagliptin ethanedisulfonate Form I, said process comprising contacting sitagliptin with ethanedisulfonic acid, optionally in the presence of a suitable solvent, and removing the solvent when necessary.

The suitable solvent comprises a $C_1$-$C_5$ alcohol solvent or mixtures thereof. Preferably, the $C_1$-$C_5$ alcohol solvent is 2-propanol.

The ethanedisulfonic acid can be optionally prepared in situ from the disodium salt of ethanedisulfonic acid and hydrochloric acid.

The 1:1 salt correlation of sitagliptin ethanedisulfonate was confirmed by $^1$H NMR spectrum.

Another aspect of the present invention includes a new sitagliptin (S)-pyroglutamate salt in crystalline form (designated herein as Form I).

Figure 10:
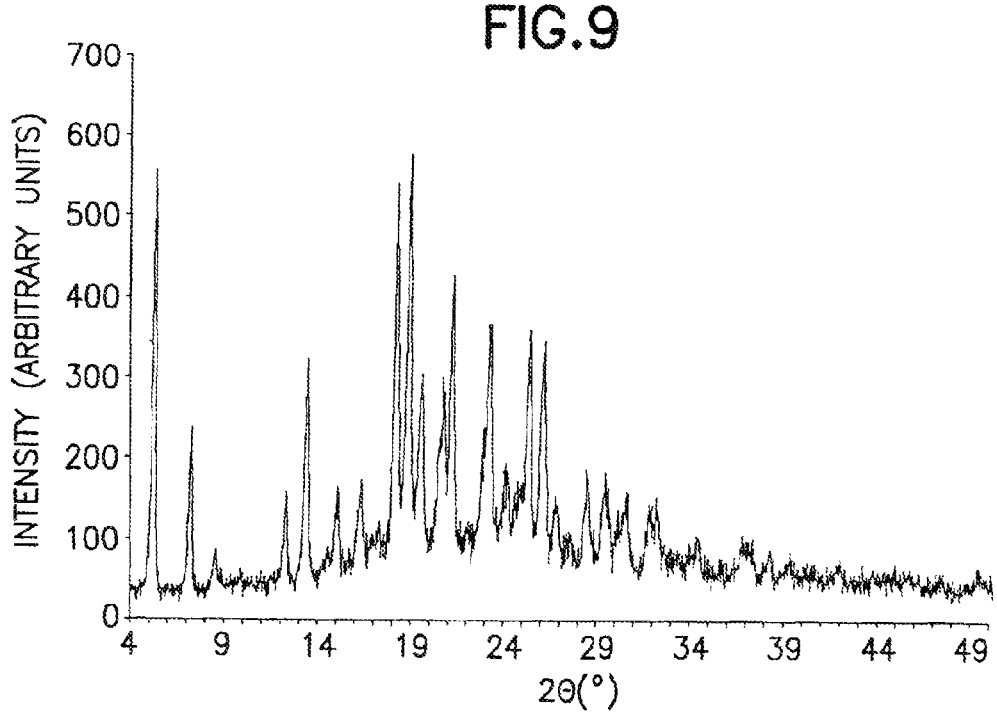
FIG. 10 illustrates the X-ray powder diffraction pattern (XRD) of sitagliptin pyroglutamate.

The sitagliptin pyroglutamate Form I of the present invention shows an XRD pattern (2θ) having characteristic peaks at approximately 5.4, 7.3, 13.5, 18.2, 18.8, 19.5, 20.6, 21.2, 23.2, 25.3 and 26.0° and with further peaks at: 12.3, 15.1, 16.3, 24.0, 26.7, 28.3, 29.4 and 30.6°. FIG. 10 illustrates the XRD of sitagliptin (S)-pyroglutamate crystalline Form I.

Another aspect of the invention relates to a process for preparing sitagliptin (S)-pyroglutamate Form I, said process comprising contacting sitagliptin with pyrrilidon-5-carboxylic acid, optionally in the presence of a suitable solvent, and removing the solvent when necessary.

The suitable solvent comprises a $C_1$-$C_5$ alcohol solvent or mixtures thereof. Preferably, the $C_1$-$C_5$ alcohol solvent is 2-propanol.

The 1:1 salt correlation of sitagliptin (S)-pyroglutamate was confirmed by $^1$H NMR spectrum.

Another aspect of the present invention includes a new sitagliptin glutarate salt in crystalline form (designated herein as Form I).

Figure 11:
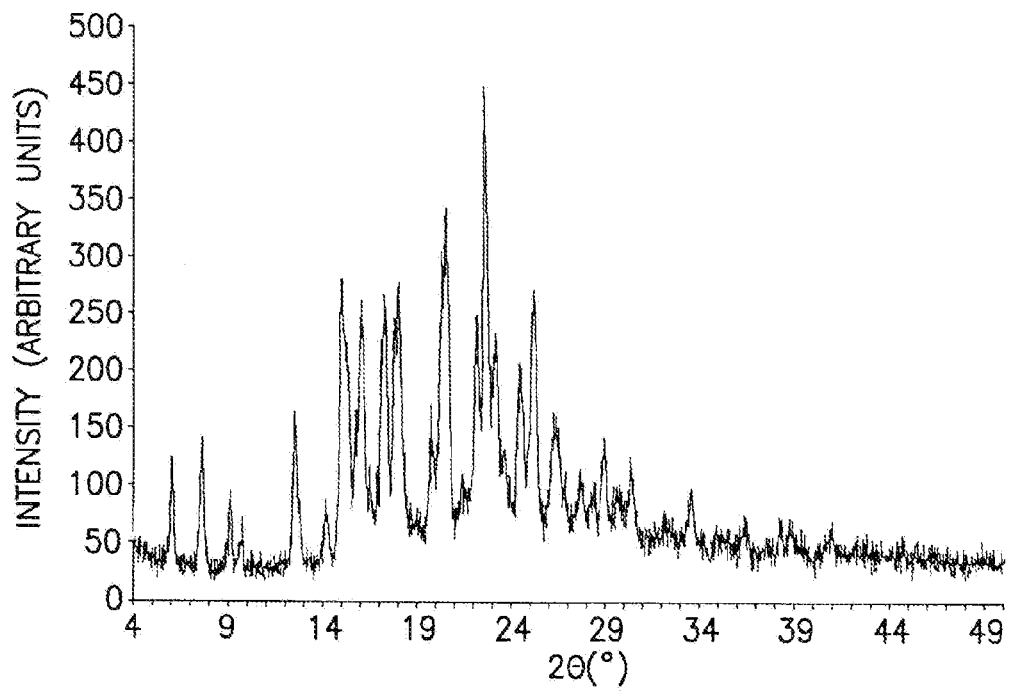
FIG. 11 illustrates the X-ray powder diffraction pattern (XRD) of sitagliptin glutarate.

The sitagliptin glutarate Form I of the present invention shows an XRD pattern (2θ) having characteristic peaks at approximately 15.3, 16.3, 17.5, 18.0, 18.3, 20.7, 22.4, 22.8, 23.4, 24.6, 25.4° and with further peaks at: 6.3, 7.9, 9.4, 12.7, 12.8, 16.7, 19.9, 26.4, 27.8, 28.5, 28.6, 29.0, 30.5, 33.8°. FIG. 11 illustrates the XRD of sitagliptin glutarate crystalline Form I.

The sitagliptin glutarate Form I of the present invention has been found to be highly stable in terms of polymorphic form after ten months of storage. Also, after ten months of storage, the sitagliptin glutarate Form I of the invention has been found to show a white colour and a purity higher than about 98.0%, as determined by HPLC.

Another aspect of the invention relates to a process for preparing sitagliptin glutarate Form I, said process comprising contacting sitagliptin with glutaric acid, optionally in the presence of a suitable solvent, and removing the solvent when necessary.

The suitable solvent comprises a $C_1$-$C_5$ alcohol solvent or mixtures thereof. Preferably, the $C_1$-$C_5$ alcohol solvent is 2-propanol.

The 1:1 salt correlation of sitagliptin glutarate was confirmed by $^1$H NMR spectrum.

Another aspect of the present invention includes a new sitagliptin acetate salt in crystalline form (designated herein as Form I).

Figure 12:
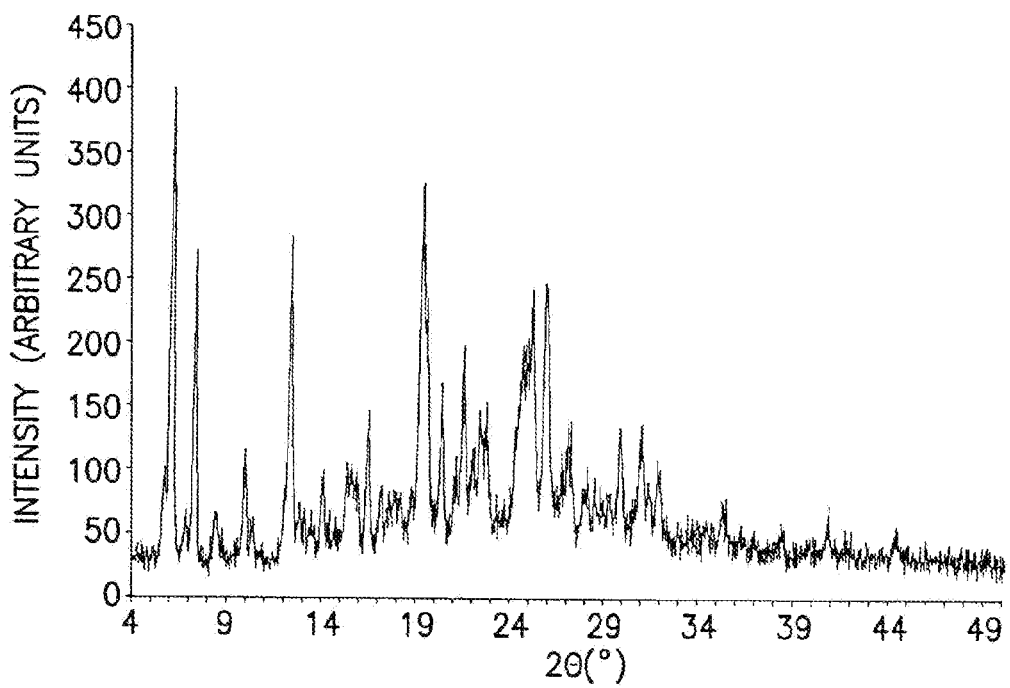
FIG. 12 illustrates the X-ray powder diffraction pattern (XRD) of sitagliptin acetate.

The sitagliptin acetate Form I of the present invention shows an XRD pattern (2θ) having characteristic peaks at approximately 6.3, 7.5, 12.5, 19.4, 19.6, 20.4, 21.6, 24.7, 25.1, 25.9 and 26.0° and with further peaks at: 10.1, 16.6, 22.4, 22.8, 27.1, 29.9, 31.0 and 31.9°. FIG. 12 illustrates the XRD of sitagliptin acetate crystalline Form I.

Another aspect of the invention relates to a process for preparing sitagliptin acetate Form I, said process comprising contacting sitagliptin with acetic acid, optionally in the presence of a suitable solvent, and removing the solvent when necessary.

The suitable solvent comprises a $C_1$-$C_5$ alcohol solvent or mixtures thereof. Preferably, the $C_1$-$C_5$ alcohol solvent is 2-propanol.

The 1:1 salt correlation of sitagliptin acetate was confirmed by $^1$H NMR spectrum.

Another aspect of the present invention includes a new sitagliptin citrate salt in amorphous form.

Figure 14:
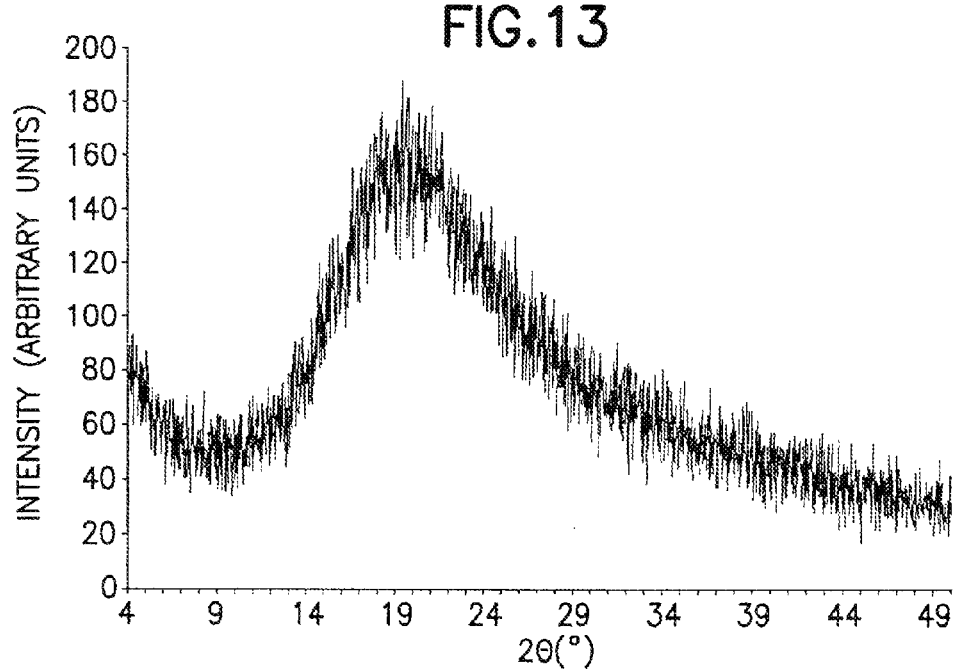
FIG. 14 illustrates the X-ray powder diffraction pattern (XRD) of sitagliptin citrate amorphous form.

The sitagliptin citrate amorphous form of the present invention shows an X-ray diffraction pattern as is substantially illustrated in FIG. 14.

Another aspect of the invention relates to a process for preparing sitagliptin citrate amorphous form, said process comprising contacting sitagliptin with at least 1 molar equivalent of citric acid, optionally in the presence of a suitable solvent, and removing the solvent when necessary.

The suitable solvent comprises a $C_1$-$C_5$ alcohol solvent or mixtures thereof. Preferably, the $C_1$-$C_5$ alcohol solvent is 2-propanol.

The 1:1 salt correlation of sitagliptin citrate was confirmed by $^1$H NMR spectrum.

Another further aspect of the present invention includes a new sitagliptin hemicitrate salt in amorphous form.

Figure 15:
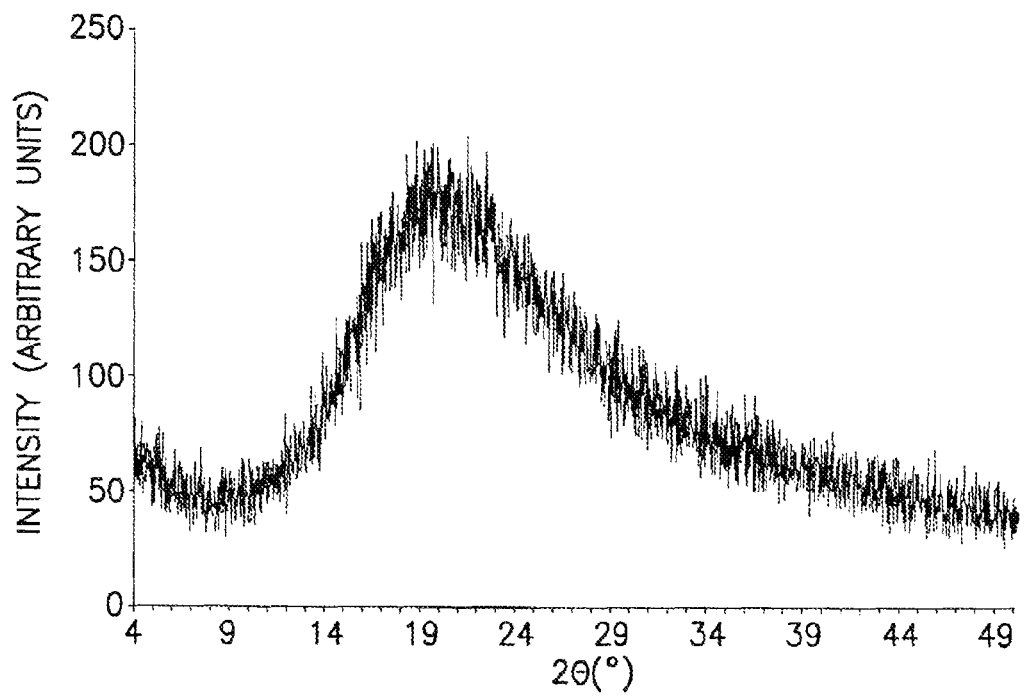
FIG. 15 illustrates the X-ray powder diffraction pattern (XRD) of sitagliptin hemicitrate amorphous form.

The sitagliptin hemicitrate amorphous form of the present invention shows an X-ray diffraction pattern as is substantially illustrated in FIG. 15.

Another further aspect of the invention relates to a process for preparing sitagliptin hemicitrate amorphous form, said process comprising contacting sitagliptin with not more than 0.5 molar equivalents of citric acid, optionally in the presence of a suitable solvent, and removing the solvent when necessary.

The suitable solvent comprises a $C_1$-$C_5$ alcohol solvent or mixtures thereof. Preferably, the $C_1$-$C_5$ alcohol solvent is 2-propanol.

The 2:1 salt correlation of sitagliptin hemicitrate was confirmed by $^1$H NMR spectrum.

Another aspect of the present invention includes a new sitagliptin glycolate salt in amorphous form.

Figure 16:
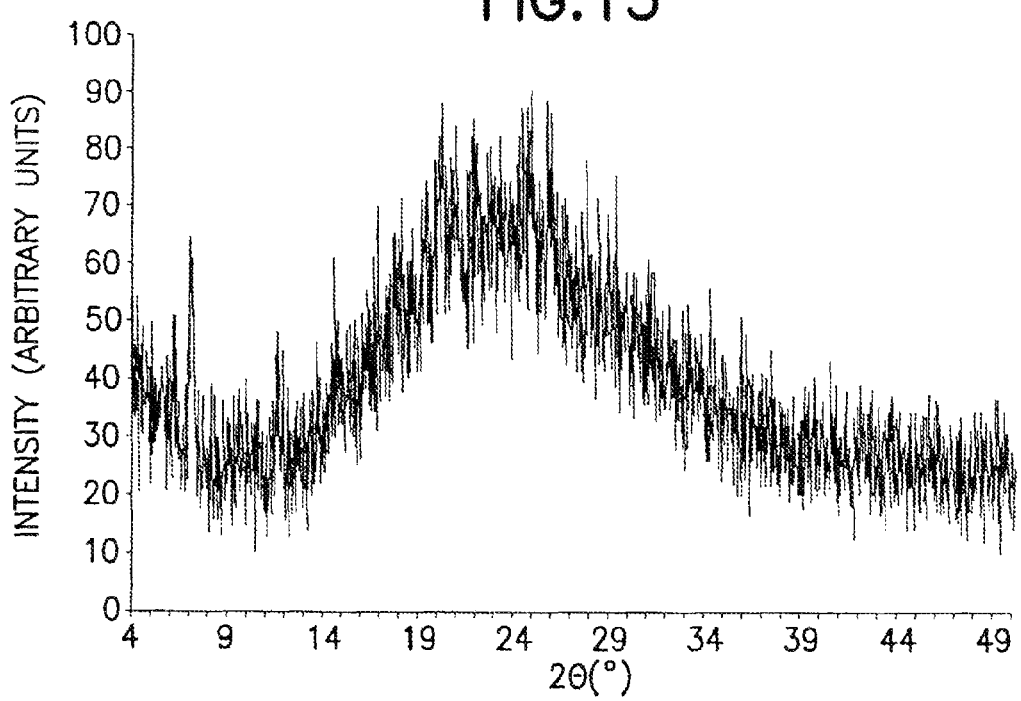
FIG. 16 illustrates the X-ray powder diffraction pattern (XRD) of sitagliptin glycolate amorphous form.

The sitagliptin glycolate amorphous form of the present invention shows an X-ray diffraction pattern as is substantially illustrated in FIG. 16.

Another further aspect of the invention relates to a process for preparing sitagliptin glycolate amorphous form, said process comprising contacting sitagliptin with glycolic acid, optionally in the presence of a suitable solvent, and removing the solvent when necessary.

The suitable solvent comprises a $C_1$-$C_5$ alcohol solvent or mixtures thereof. Preferably, the $C_1$-$C_5$ alcohol solvent is 2-propanol.

The 1:1 salt correlation of sitagliptin glycolate was confirmed by $^1$H NMR spectrum.

Another aspect of the present invention includes a new sitagliptin L-malate salt in amorphous form.

Figure 17:
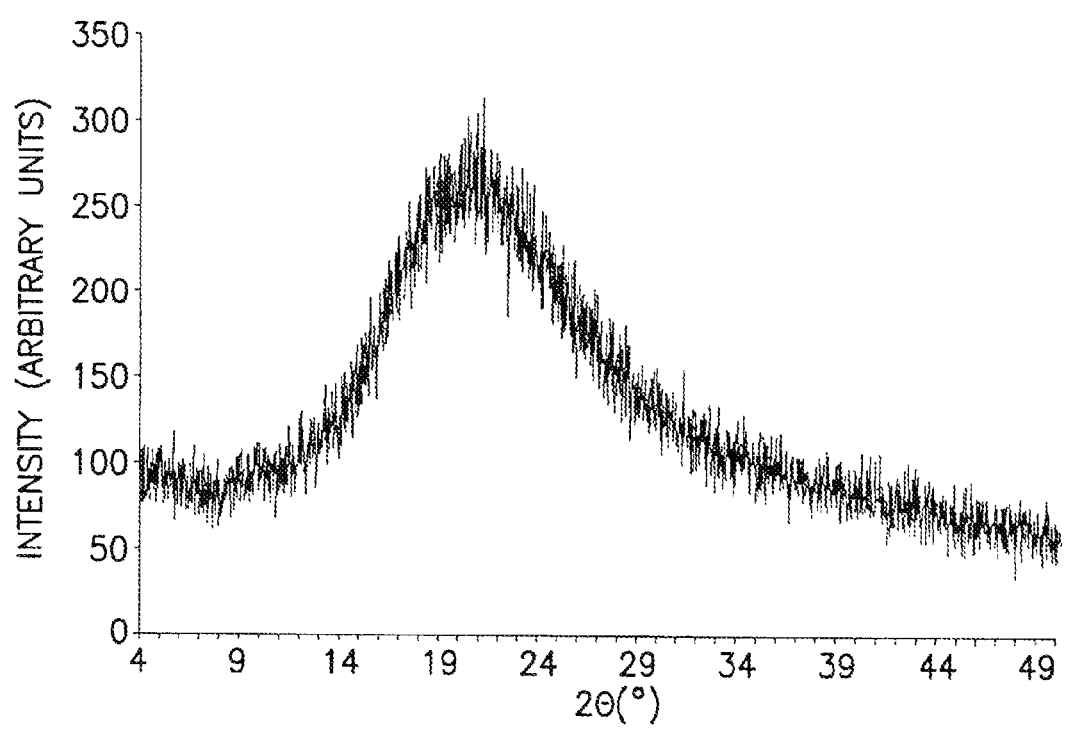
FIG. 17 illustrates the X-ray powder diffraction pattern (XRD) of sitagliptin malate amorphous form.

The sitagliptin L-malate amorphous form of the present invention shows an X-ray diffraction pattern as is substantially illustrated in FIG. 17.

Another further aspect of the invention relates to a process for preparing sitagliptin L-malate amorphous form, said process comprising contacting sitagliptin with L-malic acid, optionally in the presence of a suitable solvent, and removing the solvent when necessary.

The suitable solvent comprises a $C_1$-$C_5$ alcohol solvent or mixtures thereof. Preferably, the $C_1$-$C_5$ alcohol solvent is 2-propanol.

The 1:1 salt correlation of sitagliptin L-malate was confirmed by $^1$H NMR spectrum.

Another feature of the invention is to provide a pharmaceutical composition comprising the sitagliptin crystalline form salts of the invention.

SPECIFIC EXAMPLES

General Experimental Conditions

X-Ray Powder Diffraction (XRD)

The XRD diffractograms were obtained using a RX SIEMENS D5000 diffractometer with a vertical goniometer, a copper anodic tube, and radiation CuKα, λ=1.54056.

HPLC Method

The chromatographic separation was carried out with a Waters Sunfire C18 5 μm 4.6×250 mm column at 30° C. Mobile phase A was a mixture of methanol and 5 mM dibasic sodium phosphate buffer, pH=7.0 (70:30, v/v). The buffer was prepared by dissolving 0.217 g of dibasic sodium phosphate in 300 mL of water and adjusting the pH of the solution to 7.0±0.1 with phosphoric acid, and filtered through a 0.22 μm nylon membrane under vacuum. Mobile phase B was methanol.

The flow rate was 1 mL per minute and the chromatograph was recorded at 254 nm. Test samples (10 μL) were prepared by dissolving the appropriate amount of sample in methanol in order to obtain 1 mg of sample per mL. The following gradient was used:

| Time (min.) | % A | % B |
|---|---|---|
| 0 | 100 | 0 |
| 26 | 100 | 0 |
| 36 | 90 | 10 |
| 70 | 90 | 10 |
| 80 | 100 | 0 |
| 90 | 100 | 0 |

Examples 1-4

Preparation of Sitagliptin Salt Forms

General procedure: sitagliptin base (150 mg) was suspended in 2-propanol (2.5 mL). The acid (quantity indicated in Table 1 below) was added and the mixture was stirred for one hour at ambient temperature and 2 hours at 40° C. The mixture was allowed to cool to ambient temperature and stirred for 24 hours at this temperature. The solid was filtered and dried at ambient temperature.

TABLE 1

| Example | Acid | Quantity | Sitagliptin salt form | XRD |
|---|---|---|---|---|
| 1 | Galactaric acid | 77 mg | Sitagliptin galactarate | FIG. 1 |
| 2 | L-Malic acid | 25 mg | Sitagliptin hemi-L-malate | FIG. 2 |
| 3 | D-Gluconic acid 50% water | 145 mg | Sitagliptin D-gluconate | FIG. 3 |
| 4 | Succinic acid | 44 mg | Sitagliptin succinate | FIG. 4 |

Examples 5-12

Preparation of Sitagliptin Salt Forms

General procedure: sitagliptin base (150 mg) was suspended in 2-propanol (2.5 mL). The acid (quantity indicated in Table 2 below) was added and the mixture was stirred for one hour at ambient temperature and 2 hours at 40° C. The mixture was allowed to cool to ambient temperature and stirred for 24 hours at this temperature. The mixture was concentrated under vacuum at ambient temperature.

TABLE 2

| Example | Acid | Quantity | Sitagliptin salt form | XRD |
|---|---|---|---|---|
| 5 | Hydrobromic acid 48% | 62 mg | Sitagliptin hydrobromide | FIG. 5 |
| 6 | Thiocyanic acid disodium salt* | 30 mg | Sitagliptin thiocyanate | FIG. 6 |
| 7 | Oxalic acid (anhydrous) | 33 mg | Sitagliptin oxalate | FIG. 7 |
| 8 | L-Aspartic acid | 49 mg | Sitagliptin aspartate | FIG. 8 |
| 9 | Ethanedisulfonic acid disodium salt** | 86 mg | Sitagliptin ethanedisulfonate | FIG. 9 |
| 10 | Pyrrolidinon-5-carboxylic acid | 47 mg | Sitagliptin pyroglutamate | FIG. 10 |
| 11 | Glutaric acid | 48 mg | Sitagliptin glutarate | FIG. 11 |
| 12 | Acetic acid | 22 mg | Sitagliptin acetate | FIG. 12 |

Note:
*36 mg of HCl (37% aqueous) was also added.
**73 mg of HCl (37% aqueous) was also added.

Example 13

Preparation of Sitagliptin Hydrochloride Amorphous Form

Sitagliptin base (150 mg) was suspended in 2-propanol (2.5 mL). Hydrochloric acid (36 mg of 37% aqueous solution) was added and the mixture was stirred for one hour at ambient temperature and 2 hours at 40° C. The mixture was allowed to cool to ambient temperature and stirred for 24 hours before evaporation of the solvent.

Figure 13:
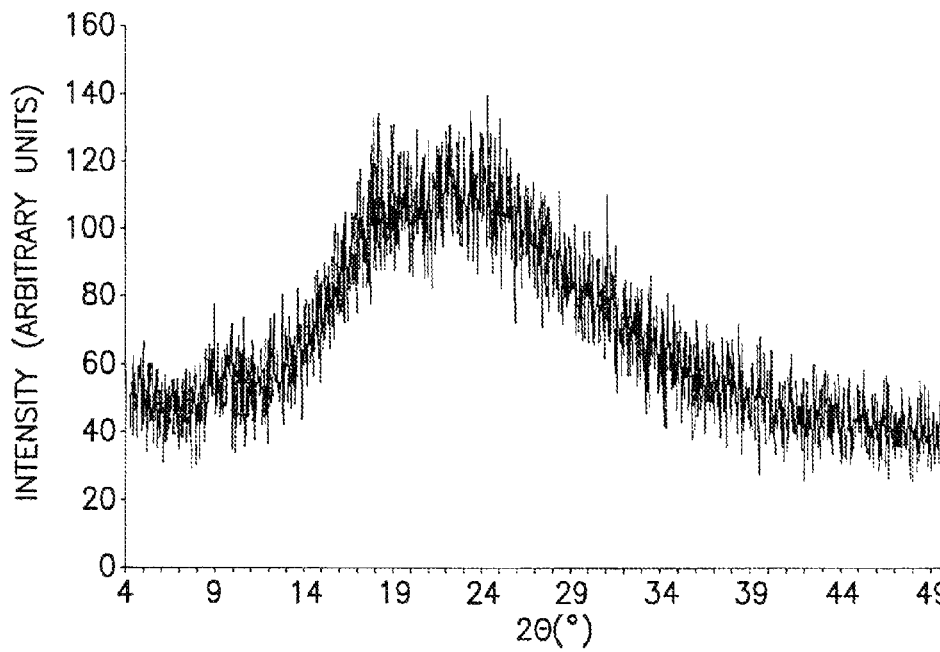
FIG. 13 illustrates the X-ray powder diffraction pattern (XRD) of sitagliptin hydrochloride amorphous form.

Analytical data: XRD: amorphous form, see FIG. 13.

Example 14

Preparation of Sitagliptin Citrate Amorphous Form

Sitagliptin base (150 mg) was suspended in 2-propanol (2.5 mL). Citric acid (71 mg) was added and the mixture was stirred for one hour at ambient temperature and 2 hours at 40° C. The mixture was allowed to cool to ambient temperature and stirred for 24 hours at this temperature. The solid was filtered and dried at ambient temperature.

Analytical data: XRD: amorphous form, see FIG. 14.

Example 15

Preparation of Sitagliptin Hemicitrate Amorphous Form

Sitagliptin base (150 mg) was suspended in 2-propanol (2.5 mL). Citric acid (35 mg) was added and the mixture was stirred for one hour at ambient temperature and 2 hours at 40° C. The mixture was allowed to cool to ambient temperature and stirred for 24 hours at this temperature. The solid was filtered and dried at ambient temperature.

Analytical data: XRD: amorphous form, see FIG. 15.

Example 16

Preparation of Sitagliptin Glycolate Amorphous Form

Sitagliptin base (150 mg) was suspended in 2-propanol (2.5 mL). Glycolic acid (28 mg) was added and the mixture was stirred for one hour at ambient temperature and 2 hours at 40° C. to give a solution. The mixture was allowed to cool to ambient temperature and stirred for 24 hours at this temperature. The solution was concentrated under vacuum at ambient temperature.

Analytical data: XRD: amorphous form, see FIG. 16.

Example 17

Preparation of Sitagliptin L-Malate Amorphous Form

Sitagliptin base (150 mg) was suspended in 2-propanol (2.5 mL). L-malic acid (49 mg) was added and the mixture was stirred for one hour at ambient temperature and 2 hours at 40° C. The mixture was allowed to cool to ambient temperature and stirred for 24 hours at this temperature. The solid was filtered and dried at ambient temperature.

Analytical data: XRD: amorphous form, see FIG. 17.

Example 18

Stability Studies of Sitagliptin Salts

Sitagliptin salts were stored under standard conditions (i.e. room temperature, normal pressure, and ambient atmosphere). The samples were analyzed after 10 months by HPLC, XRD, and visual inspection. Results are summarized in Table 3.

TABLE 3

| SITAGLIPTIN SALT | Aspect/Colour Initial | Aspect/Colour 10 months later | XRD analysis Initial | XRD analysis 10 months later | Purity (HPLC) Initial | Purity (HPLC) 10 months later |
|---|---|---|---|---|---|---|
| Galactarate | n.d.$^a$ | off-white | Form I | Form I | n.d.$^a$ | 99.15% |
| Hemi-L-malate | n.d.$^a$ | light yellow | Form I | n.d.$^a$ | n.d.$^a$ | 98.91% |
| D-Gluconate | n.d.$^a$ | beige | Form I | n.d.$^a$ | n.d.$^a$ | 96.29% |
| Succinate | n.d.$^a$ | off-white | Form I | n.d.$^a$ | n.d.$^a$ | 98.88% |
| Hydrobromide | n.d.$^a$ | off-white | Form I | Form I | n.d.$^a$ | 98.92% |
| Thiocyanate | n.d.$^a$ | light pink | Form I | Form I | n.d.$^a$ | 99.22% |
| Oxalate | n.d.$^a$ | white | Form I | Form I | n.d.$^a$ | 95.95% |
| L-aspartate | n.d.$^a$ | white | Form I | Different form | n.d.$^a$ | 97.14% |
| Ethane-disulfonate | n.d.$^a$ | off-white | Form I | Form I | n.d.$^a$ | 99.83% |
| Pyroglutamate | n.d.$^a$ | off-white | Form I | Different form | n.d.$^a$ | 98.64% |
| Glutarate | n.d.$^a$ | white | Form I | Form I | n.d.$^a$ | 98.50% |
| Acetate | n.d.$^a$ | off-white | Form I | n.d.$^a$ | n.d.$^a$ | 98.90% |

$^a$Not determined.

Example 19

Solubility Studies in Water of Sitagliptin Salts

Sitagliptin salts were suspended in water under standard conditions (i.e. room temperature, normal pressure, and ambient atmosphere), stirred until equilibration and filtered. The mother liquors were analyzed by HPLC. Results are summarized in Table 4.

TABLE 4

| Sitagliptin salt | Solubility (g/L) | Descriptive term |
|---|---|---|
| Galactarate | About 20 | Sparingly soluble |
| Ethanedisulfonate | >300 | Freely soluble |

What is claimed is:

1. Crystalline sitagliptin ethanedisulfonate salt represented by the formula:

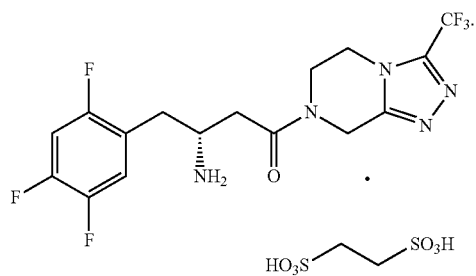 [SMILES: N[C@@H](CC(=O)N1CCn2c(nnc2C(F)(F)F)C1)Cc1cc(F)c(F)cc1F ; O=S(=O)(O)CCS(=O)(=O)O]

2. A method for treating type 2 diabetes in a subject, the method comprising administering to the subject in need thereof a therapeutically effective amount of crystalline sitagliptin ethanedisulfonate salt.

* * * * *